United States Patent
Greindl et al.

(10) Patent No.: US 6,861,548 B2
(45) Date of Patent: Mar. 1, 2005

(54) CONTINUOUS PROCESS FOR THE CYANOALKYLATION OF COMPOUNDS HAVING ONE OR MORE NH FUNCTIONS

(75) Inventors: Thomas Greindl, Bad Duerkheim (DE); Gerold Braun, Ludwigshafen (DE); Friedrich Wirsing, Speyer (DE); Georg Krug, Moerlenbach (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 129 days.

(21) Appl. No.: 10/236,904

(22) Filed: Sep. 9, 2002

(65) Prior Publication Data

US 2003/0114700 A1 Jun. 19, 2003

Related U.S. Application Data

(63) Continuation of application No. 09/970,937, filed on Oct. 5, 2001, now abandoned.

(30) Foreign Application Priority Data

Oct. 16, 2000 (DE) .......................................... 100 51 196

(51) Int. Cl.⁷ ........................................... C07C 253/22

(52) U.S. Cl. ..................................................... 558/346
(58) Field of Search ................................ 558/346, 315, 558/318

(56) References Cited

U.S. PATENT DOCUMENTS

| 3,463,805 | A | * | 8/1969 | Morgan et al. | .......... 260/465.5 |
| 3,907,858 | A | * | 9/1975 | Davis et al. | ............. 260/465.5 |
| 3,925,448 | A | | 12/1975 | Lanier | |
| 4,731,465 | A | | 3/1988 | Shen et al. | |
| 4,948,909 | A | | 8/1990 | Koenig et al. | |

FOREIGN PATENT DOCUMENTS

EP 0 102 936 3/1984

* cited by examiner

*Primary Examiner*—Joseph K. McKane
*Assistant Examiner*—Golam M M Shameem
(74) *Attorney, Agent, or Firm*—Oblon, Spivak, McClelland, Maier & Neustadt, P.C.

(57) ABSTRACT

The invention relates to a continuous process, carried out in two steps, for the cyanoalkylation of compounds having one or more NH functions by reaction thereof with carbonyl compounds and hydrocyanic acid, in which the first step is carried out without pressure at a temperature which is below the boiling point of the reaction mixture.

30 Claims, 1 Drawing Sheet

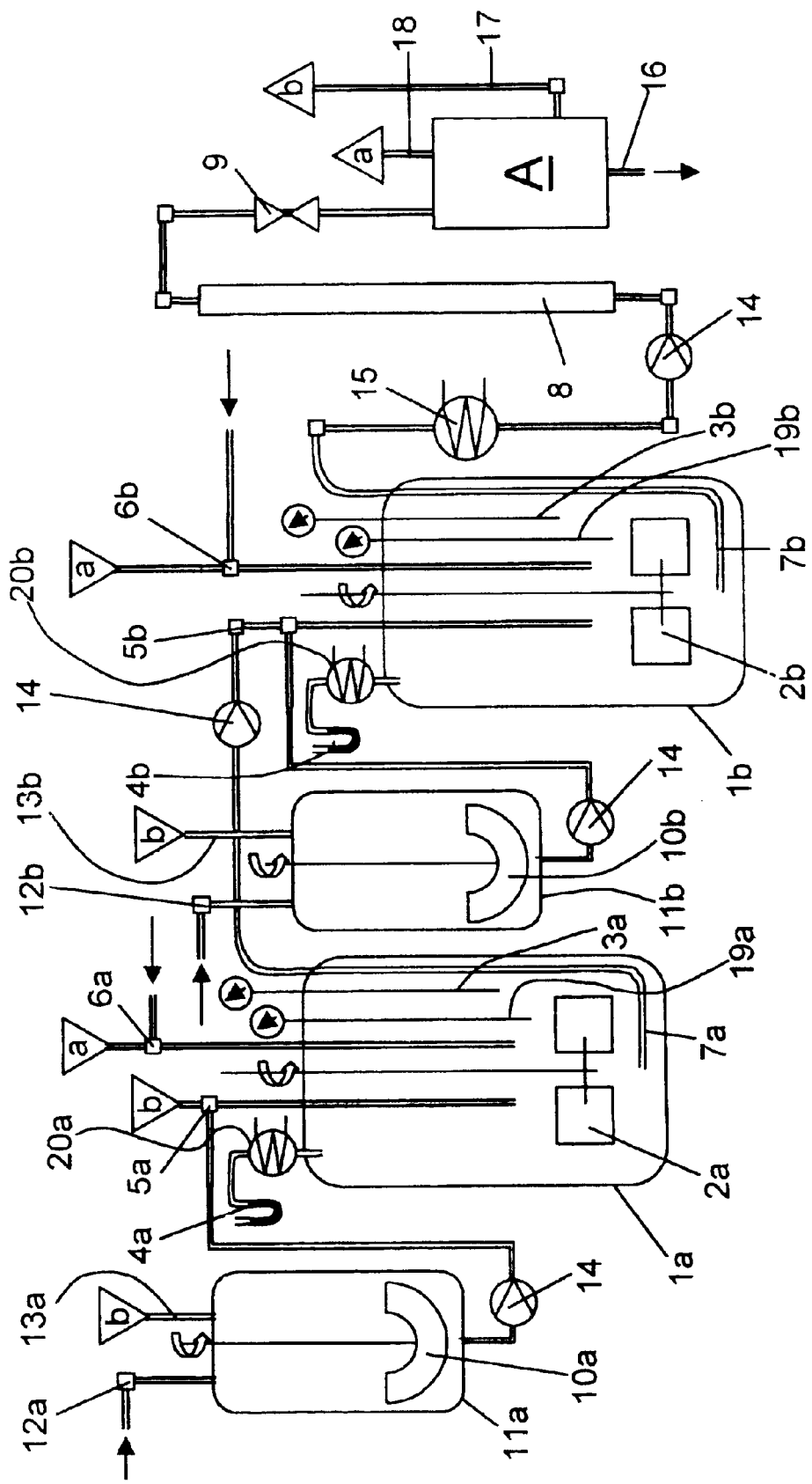

CONTINUOUS PROCESS FOR THE CYANOALKYLATION OF COMPOUNDS HAVING ONE OR MORE NH FUNCTIONS

This application is a Continuation of application Ser. No. 09/970,937 Filed on Oct. 5, 2001 now abandoned.

The present invention relates to a two-step continuous process for the cyanoalkylation of compounds having one or more NH functions by reaction thereof with carbonyl compounds and hydrocyanic acid, in which the first step is carried out without pressure at a temperature below the boiling point of the reaction mixture.

It is known to cyanoalkylate NH functions using carbonyl compounds and hydrocyanic acid. The cyanoalkylation reaction proceeds in accordance with the following scheme:

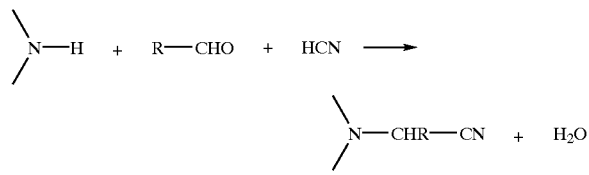

The reaction is highly exothermic, and the reaction rate increases with increasing temperature.

In the case of compounds having a plurality of NH functions, all the NH functions present can be cyanoalkylated; however, it is in principle also possible, through suitable choice of the reaction conditions, to react selectively only some of the NH functions present. Thus, for example, it is possible to convert ammonia into nitrilotriacetonitrile $N(CH_2CN)_3$ or iminodiacetonitrile $HN(CH_2CN)_2$.

A number of compounds which can be prepared by cyanoalkylation have achieved considerable industrial importance. They open up a route to the preparation of aminocarboxylic acids and in particular of nitrogen-containing polycarboxylic acids, which are widely employed as complexing agents, for example in the production of detergents.

Numerous proposals have already been published for the large industrial-scale production of cyanoalkylamino compounds. In particular, efforts have been made to increase the yields, since even relatively small increases in the yield may be accompanied by considerable economic advantages given the large quantities produced industrially. Efforts have also been made to simplify the process, in particular it has also already been attempted to carry out the preparation of cyano-alkylamines in a continuous manner.

Owing to its very considerable industrial importance, continuous processes have been proposed, in particular, for the preparation of nitrilotriacetonitrile (NTN).

U.S. Pat. No. 3,907,858 disclosed a continuous process for the preparation of NTN which uses a tubular reactor at temperatures above 120° C. and pressures of from 135 to 790 kPa. However, considerable corrosion problems arise in this process, and in addition the yield is unsatisfactory since under these conditions hydrolysis of the cyano groups already occurs to a considerable extent or other side reactions, such as multiple cyanomethylations and reductive methylations, also occur.

In a process disclosed in U.S. Pat. No. 3,463,805, the reaction is carried out adiabatically in a tubular reactor, where, starting from an initial temperature of between 0 and 130° C., a temperature increase of from 50 to 100° C. and a pressure increase of from 100 to 300 kPa occur. In a variant of this process, some of the heat being liberated is used for prewarming the starting materials. This process has the considerable disadvantage that it is very difficult to control and, through a positive back-coupling effect, can break well out of the desired reaction range. This then has the consequence not only of an impairment in the quantity and quality of the resultant product, but can also result in safety problems.

A three-step continuous process is disclosed in U.S. Pat. No. 3,925,448, in which ammonium sulfate is reacted with formaldehyde in the first step, the product from the first step is reacted with hydrocyanic acid at 93° C. in the second step, in each case in a recirculating loop reactor, and a post-reaction is subsequently carried out. However, the yield in this process is only about 90% of theory.

EP-B-0 102 936 discloses a further process for the preparation of NTN. In this process, a mixture of hexamethylenetetraamine, formaldehyde and hydrocyanic acid is adjusted to a pH of below 1 and brought to reaction firstly at a temperature of from 90 to 120° C. in a reactor, preferably a loop reactor, and subsequently transferred at a temperature of from 95 to 120° C. into a tightly packed plug-flow tubular reactor. After passing through the packed tubular reactor, the reaction mixture is then fed through a return reactor before entering a crystallizer, where the crystallization of the NTN formed takes place. All reactors are designed as double-walled tubes through whose double wall flows a heat-transfer medium which is necessary for temperature regulation of the system. This process generally gives a yield of from about 88 to 93%. The yield can, based on ammonia, be increased to about 97.5% if a hydrocyanic acid excess of from 16 to 17% is employed. The use of such a high hydrocyanic acid excess is a very considerable disadvantage for an industrial process. As a further disadvantage of this process, mention may be made of the considerable investment costs for double-walled reactors and the systems for temperature control.

We have found, surprisingly, that it is possible to carry out cyanoalkylations with comparatively low technical complexity and in very good yields if the majority of the reaction is carried out at relatively low temperature in a non-pressurized system and only the remaining conversion is carried out in a simple tubular reactor without active supply or dissipation of heat.

BRIEF DESCRIPTION OF THE DRAWING

The FIGURE diagrammatically depicts the cyanoalkylation process shown in the working examples below.

The present invention thus relates to a process for the cyanoalkylation of ammonia or organic compounds having one or more NH functions by reaction of said compounds with one mole of a carbonyl compound per NH function to be reacted and with one mole of hydrocyanic acid per NH function to be reacted, in a suitable solvent, which comprises carrying out the reaction in two sections, where the reaction in the first section is carried out to a degree of conversion of at least 60%, based on hydrocyanic acid, at a temperature $T_1$ which is below the boiling point of the reaction mixture, and the reaction in the second section is carried out to a degree of conversion of at least 90%, based on hydrocyanic acid, at a temperature $T_2$ which is below 150° C.

For the purposes of the present invention, NH functions are all direct bonds of a hydrogen atom to a nitrogen atom. A nitrogen atom can have up to three NH functions ($NH_3$); an $—NH_2$ group has two, and an $=NH$ group has one NH function. The nitrogen atoms of compounds having a plurality of nitrogen atoms can of course have different numbers of NH functions, where the number of NH functions present on the individual N atoms can be zero, one or two. Compounds having a plurality of NH functions can contain these on the same or different N atoms which may be present in the molecule.

The reaction component containing NH functions employed in the process according to the invention is a compound of the formula I

$$R_a\text{—}NH_{(3-a)} \qquad (I)$$

where R is a substituted or unsubstituted linear, branched or cyclic alkyl radical having 1 to 8 carbon atoms or aryl having 6 to 10 carbon atoms, a is one of the numbers 0, 1 or 2, and the compound of the formula I has a total of from 1 to 8 carbon atoms.

R in the formula I is preferably linear alkyl having 1 to 4 carbon atoms, in particular 1 or 2 carbon atoms, or is phenyl. The index a is preferably 1 or 2 if R is alkyl and the number 1 if R is an aryl radical.

If the compound of the formula I contains 2 radicals R, these may be identical or different within the scope of the definition given. They can differ in respect of their chain lengths, their structure (linear, branched or cyclic, aliphatic or aromatic) and/or their substituents.

Furthermore, two radicals R may also be linked to one another so that the NH function becomes part of a ring structure. The radicals R can be linked either by a direct bond or by a two-member bridge. Suitable and preferred two-member bridges are, for example, —$CH_2$—, —$NR^3$— ($R^3$=hydrogen or alkyl having 1 to 4 carbon atoms) or —O—. The resultant rings preferably have 5 to 7 members.

Suitable substituents of the alkyl groups as R are the carboxyl group and salts thereof, the cyano group, an amino group —NH—$R^1$, in which $R^1$ is hydrogen or alkyl having 1 to 4 carbon atoms, preferably 1 or 2 carbon atoms, alkoxy having 1 to 4 carbon atoms or alkylmercapto having 1 to 4 carbon atoms. Preferred substituents for R are the carboxyl or carboxylate group and the cyano group.

Examples of compounds of the formula I which are very highly suitable for conversion by the process according to the invention and result in products which are particularly important on an industrial scale are ammonia ($NH_3$), monomethylamine ($CH_3NH_2$), dimethylamine (($CH_3)_2NH$), mono- and diethylamine ($C_2H_5NH_2$,($C_2H_5)_2NH$), aminoacetonitrile (NC—$CH_2$—$NH_2$), iminodiacetonitrile (HN—($CH_2$—$CN)_2$), amino acids, for example glycine ($H_2N$—$CH_2$—COOH), N-alkylglycine, alanine ($CH_3$—$CH(NH_2)$—COOH) or N-alkylalanine, N-cyanomethylalanine (NC—$CH_2$—NH—$CH(CH_3)$—COOH), hexamethyleneimine, piperidine, piperazine, pyrrolidine and morpholine.

1,2-diaminoethane ($H_2N$—$CH_2CH_2$—$NH_2$) and its N-mono-, N-di- or N-trisubstitution products can likewise be employed if note is taken of the temperature sensitivity of the corresponding nitriles.

It is of course also possible to react a plurality of different compounds of the formula I as a mixture or one after the other. Corresponding unpurified crude products or mother liquors of these compounds can also be employed. This applies in particular to mother liquors which are formed after the end product has been separated off and are re-employed, in full or part, in the synthesis for the purposes of increasing the yield.

The carbonyl compound employed in the process according to the invention is an aldehyde of the formula II

$$R^2\text{—CHO} \qquad (II)$$

where $R^2$ is hydrogen or a substituted or unsubstituted linear or branched alkyl radical having 1 to 6 carbon atoms, preferably 1 to 3 carbon atoms, in particular 1 or 2 carbon atoms.

The carbonyl compound employed is preferably formaldehyde, acetaldehyde or propionaldehyde.

The two reaction sections are carried out in reactors connected in series.

The first reaction section is carried out in one or more cascaded, unpressurized reactors. The unpressurized reactors are advantageously boiler reactors provided with mixing devices (for example stirrers and, if desired, baffles) and devices for temperature and pH regulation.

In particular, mixing devices, for example high-speed disk or propeller stirrers, are present which allow crystallizates forming to be distributed as homogeneously as possible.

In the first reaction section, the reaction is preferably carried out to a degree of conversion of from 60 to 85%, preferably from 70 to 80%, for which a residence time of from 10 to 400 minutes, preferably from 10 to 250 minutes, in particular from 20 to 200 minutes, is necessary under the reaction conditions described above.

The second reaction section is carried out in one or more cascaded, pressurized reactors. In the second reaction section, the reaction is carried out to a degree of conversion of from 90 to 100%, preferably from 95 to 100%. In order to achieve this desired degree of conversion, a residence time of from 1 to 60 minutes, preferably from 2 to 20 minutes, in particular from 5 to 15 minutes, is set for the second reaction section. The requisite residence time also depends on the structure of the compounds employed and of the target product and can be optimized within the stated limits by means of a few preliminary experiments.

The second reaction section is preferably carried out using tubular reactors, which are advantageously provided with internals for preventing back-mixing. In particular, they are designed in such a way that, if necessary, the through-flow of emulsions and suspensions is also possible, i.e. that the internals, besides preventing back-mixing, also allow the reaction of inhomogeneous reaction mixtures.

Through this measure, particularly high conversion rates can be achieved. It is therefore particularly advantageous for the preparation of valuable commercial-scale products of relatively low solubility, for example nitrilotriacetonitrile.

Internals which have proven particularly advantageous are perforated plates. If inhomogeneous reaction mixtures are reacted further in the second reaction step, the flow rate is advantageously regulated in such a way that shear forces arise in the region of the holes of the perforated plates which prevent settling of inhomogeneities or effect dissolution of deposits present. At the same time, the design of the perforated plates is intended to prevent an unnecessarily large increase in the pressure losses into technically unfavorable regions.

The holes in the perforated plates should preferably be arranged and dimensioned in such a way that the formation of core flow is suppressed and a substantially uniform flow rate over the entire cross section of the reactor is generated.

The reduction in cross section in the perforated plates is preferably in the range from 10 to 95%, in particular from 20 to 80%, and the hole diameters preferably vary in the range from 0.1 to 10 mm, in particular from 1 to 5 mm.

As an alternative to the perforated plates, it is also possible to employ packing which causes only a slight reduction in the overall cross section and leaves sufficiently large cavities, for example beads or grit packing or packing comprising sieve or Raschig rings.

It is also possible in the process according to the invention to use different flow rates at different times, controlled, if desired, by an empirical program.

The choice of the temperature $T_1$, which is generally between 10° C. and the boiling point of the reacting mixture, preferably between room temperature (20–25° C.) and a temperature at which significant losses of hydrocyanic acid due to evaporation still do not occur, depends on the specific objective. In general, $T_1$ is below 85° C. Preference is given to temperatures of from 30 to 60° C.

If, in a starting compound having a plurality of NH groups, only a certain number of the NH functions is cyanoalkylated, the lowest possible temperature $T_1$ is advantageously selected, resulting in an increase in the selectivity of the cyanoalkylation. The formation of more highly cyanoalkylated compounds and the further reaction of product already formed, for example with hydrolysis to give amide structures, is thus kept as low as possible. On the other hand, a low temperature naturally also results in a reduction in the reaction rate, which is compensated for by an extension of the reaction time, i.e. by an extension of the residence time of the reaction mixture in the reactors. The temperature $T_2$ is generally between $T_1$ and 150° C. The same principles apply to the choice of the temperature in specific individual cases as apply to the choice of the temperature $T_1$. An advantage generally arises through a relatively low temperature $T_2$ in the preparation of products in which only some of the NH functions present are to be cyanoalkylated, in the preparation of heat-sensitive products and in systems with dominant thermodynamic reaction control.

In principle, $T_2$ can also be below $T_1$. The prerequisite for this is that the solubility or dispersibility of all components of the reaction mixture allow the reaction mixture to flow through the internals of the tubular reactor(s) without interference. In the case where a lowering of the temperature $T_2$ compared with $T_1$ is necessary or favorable, the length of the tubular reactor is advantageously increased in order to achieve the desired high degree of conversion.

A particular advantage of the process according to the invention which facilitates a particularly simple design of the reactors consists in that the second reaction section can be carried out without active supply and dissipation of heat. So long as the tubular reactor is operated at a temperature above $T_1$, self-warming of the reaction mixture can be utilized for the desired increase in temperature. It is then advantageous to reduce the heat dissipation, if necessary, by known, suitable heat-insulation measures. Alternatively, the product stream can of course also be warmed to the raised reaction temperature that may be desired before entry into the second reaction section.

Within the abovementioned limits of the reaction temperatures, the temperature range which is most suitable for the current reaction is advantageously determined in a manner known per se by means of a few preliminary experiments.

Thus, for example, it is advantageous, especially for the reaction of formaldehyde with compounds of the formula I in which a=2 and the two radicals —R are —CHR²—CN, in particular the radical the radical —CH₂—CN, to warm the product stream, advantageously to a temperature above 85° C., preferably from 95 to 135° C., in particular from 110 to 120° C., before entry into the second reaction section.

If at least one of the two radicals —R or both are radicals other than —CH₂—CN, the product stream is advantageously warmed to a temperature above 40° C., preferably from 45 to 135° C., in particular from 45 to 95° C., before entry into the second reaction section. On use of alkanals, the temperatures in the second reaction section are preferably below 100° C.

The process according to the invention can be varied in a variety of ways and matched to the needs of production and/or the properties of the starting materials and end products.

The carbonyl compound can be introduced into the reaction as such or alternatively in the form of its bisulfite adduct. Preference is given to the use of the free carbonyl compound. It is also possible to introduce the carbonyl compound and the hydrocyanic acid into the reaction in the form of the cyanohydrin of the carbonyl compound.

Furthermore, the carbonyl compound and the compound containing NH functions can be introduced into the reaction in the form of their reversibly cleavable reaction products. The compound containing NH functions can, if desired, be employed wholly or partly in the form of its salt.

A plurality of individuals of compounds containing NH functions may be involved in the reaction and either introduced into the reaction as starting materials or form during the reaction through successive cyanoalkylation of a plurality of NH functions present, which may be present on one or, if desired, on a plurality of different N atoms present in the molecule.

The various individuals can be introduced into the reaction as a mixture or successively in a planned sequence.

It is of course also possible to introduce various carbonyl compounds into the reaction if the preparation of mixtures of the target products is desired. In general, however, technically uniform starting materials are utilized for carrying out the process according to the invention.

The solvents employed for the process according to the invention can be water, lower alkanols, or mixtures thereof. The preferred solvent is water.

In order to achieve the highest possible yield of the target product, it is advantageously ensured that an adequate concentration of hydrocyanic acid is also present in the reaction mixture in the second reaction step. This does not impair the hydrocyanic acid balance of the process according to the invention, since unreacted hydrocyanic acid can be distilled off from the mother liquor and fed back into the first reaction section.

For carrying out the process according to the invention, the molar ratio between the compound containing the NH functions and the carbonyl compound employed is generally set in the range from 0.2 to 2.0, preferably from 0.3 to 1.7, in particular from 0.3 to 1.5.

However, the advantageous molar ratio to be set is highly dependent on how many of the NH functions present are to be substituted. Thus, for example, 3 mol of carbonyl compound are arithmetically required per mole of $NH_3$ for the synthesis of NTN (nitrilotriacetonitrile), while only about 1 mol of carbonyl compound is required per mole of $NH_3$ for glycine nitrile. It is therefore advantageous to base the molar ratio on the molar proportion of the NH functions to be substituted.

Although the NH function(s), the carbonyl compound and the hydrocyanic acid link to one another in the molar ratio 1:1:1 in the process according to the invention, it may in many cases be advantageous not to set this molar ratio in the reaction batch from the beginning. Rather, it may then be preferred, depending on the product to be prepared and the starting materials employed, to mix the compound containing NH functions and the carbonyl compound in a mixing ratio such that from 0.5 to 1.25, preferably from 0.6 to 1.20, in particular from 0.7 to 1.1, mole of carbonyl compound are present in the reaction mixture per mole of NH function to be reacted.

Within the stated mixing limits, the mixing ratios depend, as stated, on the current problem. If, in the case of a compound having a plurality of NH functions, only one or some are to be cyanoalkylated, the selectivity can be increased, i.e. the formation of a uniform reaction product can be significantly increased, if the reaction is carried out at the lower limits of the stated ranges. If substantially all the NH functions present in the compound are to be cyanoalkylated, the reaction is advantageously carried out in the vicinity of the upper limits of the ranges.

It is also possible and may be advantageous to carry out the metering of one or more of the reactants distributed over the reaction cascade. For example, it is possible to add only 50% of the requisite amount of one reaction component, for example the hydrocyanic acid, to the first reactor and the remaining 50% to the second reactor.

The molar ratio between the carbonyl compound and the hydrocyanic acid in the reaction system is advantageously held in the range from 0.5 to 1.2, preferably from 0.8 to 1.1, in particular from 0.95 to 1.05.

A further modification of the process according to the invention consists in firstly reacting the compound containing NH functions with the carbonyl compound and subsequently with hydrocyanic acid. This reaction sequence proves to be particularly favorable in cases where compounds containing NH functions which have a low boiling point, for example ammonia, are to be employed. Thus, for example, the cyanomethylation of $NH_3$ can be carried out particularly favorably by reaction of hydrocyanic acid with urotropin. Iminodiacetonitrile and nitrilotriacetonitrile can therefore be prepared particularly advantageously in this manner.

A further modification of the process according to the invention consists in reacting the compound containing NH functions with an adduct of the carbonyl compound and hydrocyanic acid. In many cases, this reaction also proceeds to a significant extent parallel to other cyanoalkylation reaction routes and can contribute to an increase in the yield if the adduct, which generally forms as a by-product in addition to the cyanoalkylation product, cleaves back to a sufficient extent. It is therefore advantageous to select the reaction conditions, in particular in the second reaction section, in such a way that the re-cleavage of the adduct is favored. In particular in the preparation of NTN, a significant increase in yield can be achieved by reactivation of the formaldehyde cyanohydrin.

In general, the two reaction routes, namely
1. the reaction of an addition compound of the compound containing NH functions and the carbonyl compound with hydrocyanic acid, and
2. the reaction of a compound containing NH functions with an adduct of the carbonyl compound and hydrocyanic acid, will take place simultaneously as parallel reactions during performance of the process according to the invention.

It is also possible within the scope of the invention to combine the amine, carbonyl compound and HCN simultaneously. This is particularly advantageous if substitution of only some of the NH functions present is desired. It may even be advantageous firstly to pre-mix the amine and HCN and then to add the carbonyl compound.

The hydrocyanic acid is preferably employed in free form, but can also be employed in the form of a metal salt, preferably an alkali metal salt.

Ammonia and formaldehyde can be introduced into the reaction in the form of hexamethylenetetraamine (urotropin), and ammonia and acetaldehyde can be introduced into the reaction in the form of aldehyde ammonia.

The essential advantages of the process according to the invention over other known continuous processes for the preparation of NTN, in particular also over the process disclosed in EP-B-0 102 936, lie in the increase in yield which can be achieved by means of simple technical measures and small excesses of hydrocyanic acid. Through the linking of unpressurized boiler reactors with a simple tubular reactor, the majority of the reaction can be carried out at mild temperatures and with pH maintenance. This has the advantage that undesired side reactions, in particular the hydrolysis of product that has already formed, can be substantially avoided and that a higher selectivity of the reaction is achieved, enabling the flexibility of the process to be increased very significantly, so that it can be matched to the preparation of the very wide range of cyanoalkylation products.

Another advantage in carrying out the reaction in two steps is the possibility of using a steady-state excess of hydrocyanic acid. This results in a high degree of conversion even in the first reaction step, so that the content of free hydrocyanic acid (low-boiling component and therefore a cause of pressure build-up) before entry of the reaction mixture into the tubular reactor is generally only about 1.5%. The pressures of 150 hPa at, for example, 115° C. are therefore relatively low compared with the pressures of from 500 to 600 hPa in the most comparable process (EP-B-0 102 936). Furthermore, the low proportion of residual reaction in the tubular reactor makes complex temperature control unnecessary. The temperature generally increases by not more than 5° C. This in turn makes it possible to set the reaction conditions (temperature and pressure) very precisely. This results in lower investment costs and, last but not least, greater process and plant safety, since hydrocyanic acid is handled in the lowest possible amount, at the lowest possible pressures and with the lowest possible permanent heat evolution.

The present invention also relates to the cyanoalkylation products, the α-cyanoalkylamines, prepared by the process according to the invention.

The α-cyanoalkylamines prepared in accordance with the invention are predominantly hydrolyzed to the corresponding carboxylic acids, which are used in many areas of industry, preferably as complexing agents, for example in the production of detergents. Some examples of compounds and secondary products thereof of high industrial importance which can be prepared by the process according to the invention are summarized in an overview on the next page.

The invention furthermore relates to the use of the α-cyanoalkylamines prepared in accordance with the invention as starting materials in continuing synthetic processes, in particular those whose first synthesis step consists in hydrolysis of the cyano groups to give carboxamides or carboxylic acids. Examples of syntheses of this type are the preparation of α-aminocarboxylic acids by hydrolysis of the cyano groups, the use of the N-cyanomethylaniline prepared by the process according to the invention for the preparation of indigo, the use of iminodiacetonitrile prepared in accordance with the invention for the preparation of N-phosphonomethylglycine and the use of the sarcosine nitrile prepared in accordance with the invention for the preparation of creatine and acyl sarcosinates.

| Primary starting material | Cyanoalkyl product | Industrially important secondary product |
|---|---|---|
| $NH_3$ | NC-CH2-NH-CH2-CN (di(cyanomethyl)amine) | NC-CH2-N(CH2CN)-CH2-CN (nitrilotriacetonitrile) |
| $NH_3$ | NC-CH2-N(CH2CN)-CH2-CN | $HO_2C$-CH2-N(CH2CO2H)-CH2-$CO_2H$ |
| $NH_3$ | NC-CH2-NH-CH2-CN | $HO_2C$-CH2-NH-CH2-$CO_2C$H → $HO_2C$-CH2-N($H_2O_3P$-CH2)-NH (or similar phosphonate derivative) |
| NC-CH2-NH-CH2-CN | NC-CH2-N(CH(CH3)CN)-CH2-CN | $HO_2C$-CH2-N(CH(CH3)CO2H)-CH2-$CO_2H$ |
| $H_3C-NH_2$ | $H_3C$-NH-CH2-CN | $H_3C$-NH-CH2-COOH |
| Ph-$NH_2$ (aniline) | Ph-NH-CH2-CN | Ph-NH-CH2-COOH → (indigo structure) |

The working examples below illustrate the present invention.

The laboratory trial plant shown diagrammatically and without scale and employed for carrying out the following examples consists of two cascaded 2 l four-necked glass flasks (1a, 1b) with stirrers (2a, 2b), thermometers (3a, 3b), pH electrodes (19a, 19b), paraffin-sealed fermentation tubes (4a, 4b), which are connected to the reactors via reflux condensers (20a, 20b) operated at 0° C., a feed tube (5a, 5b) each for fresh amino and carbonyl compound and, if desired, mother liquor, which extends into the center of the flask, a feed tube (6a, 6b) each for fresh and, where appropriate, recycled hydrocyanic acid which extends into the center of the flask, and an outflow tube (7a, 7b) each extending to the base, and a tubular reactor (8), which is provided with 10 perforated plates and is sealed at the outlet by a pressure retention valve (9). As an alternative to the perforated plates, packing, for example comprising sieve or Raschig rings, can also be installed in the tubular reactor.

The flasks 1a and 1b are provided with thermostatted waterbaths, which are not shown in the figure for reasons of clarity.

Furthermore, the experimental set-up also has mixing vessels (11a, 11b) provided with stirrers (10a, 10b), in which the compound containing NH functions and the carbonyl compound can be premixed with water or mother liquor before being fed into the flasks 1a and 1b. The mixing vessels have feeds (12a, 12b) for fresh reactants and for recycled mother liquor (13a, 13b).

The reaction mixture or the fresh reactant mixtures is/are conveyed by means of laboratory metering pumps (14), and for temperature adjustment of the reaction mixture before feeding into the tubular reactor, a heat exchanger (15) which can be switched in if desired is provided between the second four-necked flask and the tubular reactor.

The outlet of the tubular reactor runs into a work-up device, which is symbolized in the figure by the unit A. Depending on the current product, the work-up device consists, for example, of a coolable, stirred crystallization vessel which is sealed without pressure and to which a pressure filter is connected, and/or, for example, one or more rotary evaporators, which can be evacuated if desired, with downstream cold traps for the condensation of excess hydrocyanic acid.

The work-up device has outlets (16) for the resultant product, (17) for mother liquor to be recycled and (18) for hydrocyanic acid to be recycled.

Hydrocyanic acid can also be recovered from mother liquor (17) by subsequent distillation, for example in one of the rotary evaporators mentioned above, and fed back into the process via (18).

The work-up unit outlet denoted by a triangle standing on the base and indicated by "a" can, if necessary, be connected to the reactor inlets denoted by the triangles standing on the tip and indicated by "a", and the work-up unit outlet denoted by a triangle standing on the base and indicated by "b" can, if necessary, be connected to the reactor inlets denoted by the triangles standing on the tip and indicated by "b".

If necessary, additives for pH regulation, preferably inorganic acids, for example sulfuric acid, can also be added via the inlets denoted by triangles "b" standing on the tip. The addition takes place under pH control in connection with the pH measurements by the electrodes (19a) and (19b).

SUMMARY OF THE MEANINGS OF THE REFERENCE SYMBOLS USED IN THE FIGURE 1a,1b: four-necked glass flasks
2a,2b: stirrers
3a,3b: thermometers
4a,4b: fermentation tubes
5a,5b: feed tubes
6a,6b: feed tubes
7a,7b: outflow tubes
8: tubular reactor
9: pressure retention valve
10a,10b: stirrers
11a,11b: mixing vessels
12a,12b: feeds for fresh reactants
13a,13b: feeds for mother liquor
14: metering pumps
15: heat exchanger
16: product outlet
17: mother liquor outlet
18: hydrocyanic acid outlet
19a,19b: pH electrodes
20a,20b: reflux condensers
A: work-up unit Summary of the meanings of the reference symbols used in the figure.

| | |
|---|---|
| 1a, 2b: | four-necked glass flasks |
| 2a, 2b: | stirrers |
| 3a, 3b: | thermometers |
| 4a, 4b: | fermentation tubes |
| 5a, 5b: | feed tubes |
| 6a, 6b: | feed tubes |
| 7a, 7b: | outflow tubes |
| 8: | tubular reactor |
| 9: | pressure retention valve |
| 10a, 10b: | stirrers |
| 11a, 11b: | mixing vessels |
| 12a, 12b: | feeds for fresh reactants |
| 13a, 13b: | feeds for mother liquor |
| 14: | metering pumps |
| 15: | heat exchanger |
| 16: | product outlet |
| 17: | mother liquor outlet |
| 18: | hydrocyanic acid outlet |
| 19a, 19b: | pH electrodes |
| 20a, 20b: | reflux condensers |
| A: | work-up unit |

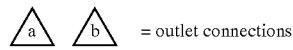 = outlet connections

-continued

Summary of the meanings of the reference symbols used in the figure.

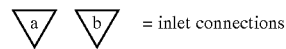 = inlet connections

EXAMPLE 1

Preparation of Iminodiacetonitrile

The first four-necked flask (1a) of the trial plant is charged with a mixture of 1412 g of 15.9% by weight aqueous hexamethylenetetramine (HMTA) solution (~140 g of HMTA)—prepared by prior reaction of 960 g of 30% by weight aqueous formaldehyde and 452 g of 25% by weight aqueous ammonia, followed by post-reaction for one hour at 50° C.—and 277 g of hydrocyanic acid (99% by weight) and held at 50° C. by cooling. A pH of 6 is maintained by addition of a total of 186 g of 50% by weight aqueous sulfuric acid.

The mixture is stirred for 60 minutes, and it is then begun to pump the flask contents over into the second flask (1b) through the outflow tube (7a) at a rate of 1800 ml per hour. At the same time, a 15.9% by weight solution of HMTA in water or mother liquor is metered into the first flask (1a) via the first feed tube (5a) from the mixer (1a) at a rate of 1410 ml per hour, and 277 g per hour of 99% hydrocyanic acid are metered in through the second feed tube (6a).

At the same time, it is begun to hold the pH in the second flask at 6.0 by addition of 50% by weight sulfuric acid.

When the feed from the first flask into the second flask has taken place for one hour, a volume of 1800 ml of reaction mixture is present in the second flask, which is likewise held at a temperature of 50° C.

It is then begun to feed the contents of this second flask into the tubular reactor (8) (length 100 cm and internal diameter 1.8 cm) from below via a heat exchanger (15), which is operated at 95° C., at a rate of 1700 to 1800 ml per hour.

The internal pressure in the reactor is set to an excess pressure of 200 hPa by means of a pressure retention valve (9). As soon as this pressure has been reached, the valve (9) opens at the outlet sufficiently far that this pressure is maintained. After 60 minutes, the reaction mixture exits from the pressure retention valve and can be worked up as follows:

Each 2 l of mixture emerging from the reactor are evaporated with constant stirring, for example in a rotary evaporator in a water-jet vacuum at 25° C., until crystallization commences and subsequently stirred at 5° C. for 30 minutes. The precipitate is filtered off with suction, and the filtrate (mother liquor) is employed for the preparation of the feed fed to the first flask. The precipitate, consisting of iminodiacetonitrile, is then washed with demineralized water and dried. The hydrocyanic acid collected in the cold trap of the rotary evaporator is weighed and fed back into the flask (1a) via feed (6a).

The yield, based on hydrocyanic acid, is 97% of theory.

EXAMPLE 2

Preparation of Nitrilotriacetonitrile

The first four-necked flask (1a) of the trial plant is charged with 1300 g of an 8.1% by weight aqueous solution of hexamethylenetetraamine—prepared by mixing 260 g of 38.5% by weight ammonium sulfate solution, 85 g of 30% by weight aqueous ammonia and 955 g of 30% by weight aqueous formaldehyde at 50° C. and post-reaction at 50° C.

for 1 hour—and 260 g of hydrocyanic acid (99%), adjusted to a pH of 0.5 by addition of 8 g of 96% by weight sulfuric acid and thermostatted at a temperature of from 40 to 50° C. The mixture is stirred for 45 minutes, and it is then begun to pump the flask contents over into the second flask (1b) through the outflow tube (7a) at a rate of 32 ml per minute. At the same time, a mixture of 1300 parts by weight of an 8.1% by weight aqueous solution of hexamethylenetetraamine and 230 parts by weight of water or mother liquor which has been adjusted to pH 0.5 by means of about 8 parts by weight of 96% by weight sulfuric acid is metered into the first flask via the first feed tube (5a) from the mixer (11a) at a rate of 25 ml per minute, and 4.3 g per minute of 99% hydrocyanic acid are metered in through the second feed tube (6a). Water or mother liquor or washing water from the product separation in the work-up vessel A is simultaneously metered into the second flask at a rate of 2 g per minute.

After 45 minutes, a volume of about 2000 ml of reaction mixture is present in the second flask, which is set to a temperature of from 50 to 60° C. It is then begun to feed the contents of this second flask into the tubular reactor (8) (length 50 cm and internal diameter 1.8 cm) from below at a rate of about 32 ml per minute. A heat exchanger (15), in which the reaction mixture flowing through is warmed to a temperature of from 110 to 115° C., is connected here between the second flask and the tubular reactor. As soon as the internal pressure of the reactor has reached 200 hPa, the pressure retention valve (9) opens at the outlet sufficiently that the pressure is maintained. After 15 minutes, the reaction mixture exits from the pressure retention valve and is collected, stirred at from 5 to 10° C. for 30 minutes and filtered in a pressure filter. The filtrate (mother liquor) is partly employed for the preparation of the feed fed to the first flask and partly distilled in order to recover excess hydrocyanic acid. The precipitate, consisting of nitrilotriaceto-nitrile, is then washed with demineralized water and dried. The recovered hydrocyanic acid is weighed and fed back into the flask (1a) via the outlet (18) and feed (6a). The yield, based on hydrocyanic acid, is 98.3% of theory.

EXAMPLE 3

Preparation of Sarcosine Nitrile

The first four-necked flask (1a) of the trial plant is charged with a solution of 326 g of monomethylamine in 489 ml of water, 732 g of a 30% by weight aqueous formaldehyde solution and 202 g of hydrocyanic acid (99%) and held at 30° C. by cooling. The mixture is stirred for 2.5 minutes, and it is then begun to pump the flask contents over into the second flask (1b) through the outflow tube (7a) at a rate of 60 ml per minute. At the same time, a mixture of 326 parts by weight of monomethylamine, 489 parts by weight of water and 732 parts by weight of a 30% by weight aqueous formaldehyde solution is metered into the first flask via the feed tube (5a) from the mixer (11a) at a rate of 53 ml per minute, and 6.7 g per minute of 99% hydrocyanic acid are metered in through the feed tube (6a).

30 minutes after commencement of the feed from the first flask into the second flask, a volume of about 1800 ml of reaction mixture is present in the second flask, which is likewise held at a temperature of 25° C. It is then begun to feed the contents of this second flask into the tubular reactor (length 60 cm and internal diameter 1.8 cm) from below via the outlet (7b) and the heat exchanger (15), which is operated at 50° C., at a rate of from 60 to 65 ml per minute. As soon as the internal pressure in the reactor has reached 200 hPa, the pressure retention valve (9) opens at the outlet sufficiently that this pressure is maintained.

After 8 to 10 minutes, the reaction mixture exits from the pressure retention valve and can be further converted directly into sarcosine in a subsequent step without further purification. The yield, based on hydrocyanic acid, is 95.7% of theory.

EXAMPLE 4

Preparation of N,N-biscyanomethyl-2-aminopropionitrile

The first four-necked flask (1a) of the trial plant is charged with 1132 g of a mixture, at 50° C., of 26% by weight of aminodiacetonitrile in mother liquor as produced in Example 1 at the outlet of the tubular reactor (or alternatively 294 g of iminodiacetonitrile in 838 g of water), 163 g of acetaldehyde and 92.8 g of hydrocyanic acid (99%), adjusted to a pH of 1.5 by addition of about 98 g of 50% by weight sulfuric acid and thermostatted to a temperature of 50° C. The mixture is stirred for 20 minutes, and it is then begun to pump the flask contents over into the second flask (1b) through the outflow tube (7a) at a rate of 75 ml per minute. At the same time, a mixture, adjusted to pH 1.5 by means of sulfuric acid, of 838 parts by weight of water or mother liquor, 294 parts by weight of iminodiacetonitrile, 98 parts by weight of 50% by weight sulfuric acid and 163 parts by weight of acetaldehyde is metered into the first flask from the mixer (11a) via the feed tube (5a) at a rate of 70 ml per minute, and 4.7 g per minute of 99% hydrocyanic acid are metered in through the second feed tube (6a).

After 20 minutes, a volume of about 1500 ml of reaction mixture is present in the second flask (1b), which is set to a temperature of from 50 to 60° C. It is then begun to feed the contents of this second flask into the tubular reactor (8) (length 50 cm and internal diameter 1.8 cm) from below at a rate of about 75 ml per minute. A heat exchanger (15), in which the reaction mixture flowing through is warmed to a temperature of 70° C., is installed here between the second flask and the tubular reactor. As soon as the internal pressure of the reactor has reached 200 hPa, the pressure retention valve (9) opens at the outlet sufficiently that this pressure is maintained. After 20 minutes, the reaction mixture exits from the pressure retention valve and is collected, stirred at 40° C. for 90 minutes and at from 5 to 10° C. for 30 minutes and filtered on a pressure filter. The filtrate (mother liquor) is partly employed for the preparation of the feed fed to the first flask and partly distilled in order to recover excess hydrocyanic acid.

The precipitate, consisting of N,N-biscyanomethyl-2-aminopropionitrile, is then washed with demineralized water and dried. The recovered hydrocyanic acid is weighed and fed back into the flask (1a). The yield, based on hydrocyanic acid, is 98.5% of theory.

We claim:

1. A process for the production of an α-cyanoalkylamine comprising:

reacting ammonia or an organic compound comprising one or more NH functions with one mole of a carbonyl compound per NH function to be reacted and with one mole of hydrocyanic acid per NH function to be reacted;

wherein said reaction comprises a first and second section, wherein the reaction in the first section is carried out in a non-pressurized system to a degree of conversion of from 60 to 85% based on hydrocyanic acid, at a temperature $T_1$ which is below the boiling point of the reaction mixture, and wherein the reaction in the second section is carried out to a degree of conversion of at least 90% based on hydrocyanic acid, at a temperature $T_2$ which is below 150° C.

2. The method of claim 1, wherein $T_2$ is between $T_1$ and 150° C.

3. The process of claim 1, comprising reacting ammonia with one mole of a carbonyl compound per NH function to be reacted and with one mole of hydrocyanic acid per NH function to be reacted.

4. The process of claim 1, comprising reacting an organic compound comprising one or more NH functions with one mole of a carbonyl compound per NH function to be reacted and with one mole of hydrocyanic acid per NH function to be reacted.

5. The process of claim 1, wherein the molar ratio of the compound containing the NH functions and the carbonyl compound ranges from 0.2 to 2.0.

6. The process of claim 1, wherein the molar ratio of the compound containing the NH functions and the carbonyl compound ranges from 0.3 to 1.5.

7. The process of claim 1, wherein the molar ratio of the carbonyl compound and the hydrocyanic acid ranges from 0.5 to 1.2.

8. The process of claim 1, wherein the molar ratio of the carbonyl compound and the hydrocyanic acid ranges from 0.95 to 1.05.

9. The process of claim 1, wherein the compound containing NH functions and the carbonyl compound are mixed in a mixing ratio such that from 0.2 to 2.0 mol of carbonyl compound are present in the reaction mixture per mole of NH function to be reacted, and the molar ratio between carbonyl compound and hydrocyanic acid in the reaction system is held in the range from 0.5 to 1.2.

10. The process of claim 1, wherein said organic compound comprises formula (I):

$$R_a\text{—}NH_{(3-a)} \qquad (I)$$

where R is a substituted or unsubstituted linear, branched or cyclic alkyl radical having 1 to 8 carbon atoms or aryl having 6 to 10 carbon atoms, a is 0, 1 or 2, and the compound of formula I has a total of 1 to 8 carbon atom(s).

11. The process of claim 10, wherein
R in formula (I) is linear alkyl having 1 to 4 carbon atoms or is phenyl,
wherein a is 1 or 2 if R is linear alkyl, or 1 if R is phenyl.

12. The process of claim 10, wherein R in formula (I) is linear alkyl having 1 to 2 carbon atom(s).

13. The process of claim 1, wherein the carbonyl compound employed is an aldehyde of formula (II):

$$R_2\text{—}CHO \qquad (II)$$

where $R_2$ is hydrogen or a substituted or unsubstituted linear or branched alkyl radical having 1 to 6 carbon atom(s).

14. The process of claim 13, wherein $R_2$ is hydrogen.

15. The process of claim 13, wherein $R_2$ is an unsubstituted linear or branched alkyl radical.

16. The process of claim 13, wherein $R_2$ is a substituted linear or branched alkyl radical.

17. The process of claim 13, wherein $R_2$ has 1 carbon atom.

18. The process of claim 13, wherein $R_2$ has 2 carbon atoms.

19. The process of claim 13, wherein $R_2$ has 3 carbon atoms.

20. The process of claim 1, wherein the carbonyl compound employed is formaldehyde, acetaldehyde or propionaldehyde.

21. The process of claim 1, wherein the first reaction section is carried out in one or more cascaded, non-pressurized reactor(s).

22. The process of claim 1, wherein the second reaction section is carried out in one or more cascaded, pressurized reactor(s) without active supply or dissipation of heat.

23. The process of claim 1, wherein the reaction in the second reaction section is carried out to a degree of conversion of from 90 to 100%.

24. The process of claim 1, wherein the second reaction section is carried out using tubular reactors which are provided with internals for reducing back-mixing.

25. The process of claim 24, wherein the tubular reactors prevent back-mixing and allow the reaction of inhomogeneous reaction mixtures.

26. An α-cyanoalkylamine prepared by the process of claim 1.

27. A method of performing a continuing synthetic process wherein an α-cyanoalkylamine prepared by the process of claim 1 is applied as a starting material.

28. The method of claim 27, wherein said continuing synthetic process comprises as its first step, hydrolysis of the cyano group to give a carboxamide or a carboxylic acid.

29. A process for the production of an α-cyanoalkylamine, other than nitrilotriacetonitrile (NTAN), comprising:
reacting ammonia or an organic compound comprising one or more NH functions with one mole of a carbonyl compound per NH function to be reacted and with one mole of hydrocyanic acid per NH function to be reacted; and
recovering the α-cyanoalkylamine other than nitrilotriacetonitrile (NTAN);
wherein said reaction comprises a first and second section,
wherein the reaction in the first section is carried out in a non-pressurized system to a degree of conversion of from 60 to 85% based on hydrocyanic acid, at a temperature $T_1$ which is below the boiling point of the reaction mixture, and
wherein the reaction in the second section is carried out to a degree of conversion of at least 90% based on hydrocyanic acid, at a temperature $T_2$ which is below 150° C.

30. The process of claim 29, wherein said second reaction section is performed in one or more tubular reactor(s) without active supply or dissipation of heat.

* * * * *